United States Patent
Caron et al.

(10) Patent No.: US 9,097,620 B2
(45) Date of Patent: Aug. 4, 2015

(54) DEFLECTION INDICATION GAUGE

(71) Applicant: APPLETON PAPER INC., Appleton, WI (US)

(72) Inventors: Kelly John Caron, Suamico, WI (US); Ruth Monica Prasetio, Appleton, WI (US)

(73) Assignee: APPVION, INC., Appleton, WI (US)

( * ) Notice: Subject to any disclaimer, the term of this patent is extended or adjusted under 35 U.S.C. 154(b) by 169 days.

(21) Appl. No.: 13/767,473

(22) Filed: Feb. 14, 2013

(65) Prior Publication Data

US 2014/0224034 A1 Aug. 14, 2014

(51) Int. Cl.
*G01N 3/20* (2006.01)
*G01N 33/34* (2006.01)

(52) U.S. Cl.
CPC .............. *G01N 3/20* (2013.01); *B65H 2220/01* (2013.01); *B65H 2515/37* (2013.01); *G01N 33/346* (2013.01); *G01N 2203/0033* (2013.01); *G01N 2203/0282* (2013.01); *G01N 2203/0682* (2013.01)

(58) Field of Classification Search
CPC ........... B65H 2515/30; B65H 2515/81; B65H 2515/37; B65H 2511/416; B65H 2511/17; B65H 2220/01; G01N 33/346; G01N 3/08; G01N 3/20; G01N 5/107; G01N 5/0038
USPC ........ 73/849, 851, 852, 854; 271/262, 265.04
See application file for complete search history.

(56) References Cited

U.S. PATENT DOCUMENTS

| | | | |
|---|---|---|---|
| 3,744,047 A | 7/1973 | Allen | |
| 3,834,031 A | 9/1974 | Muller | |
| 4,375,722 A | 3/1983 | Nishikata et al. | |
| 4,778,167 A | 10/1988 | Snow et al. | |
| 4,826,149 A | 5/1989 | Tucker | |
| 4,864,851 A * | 9/1989 | Houghton | 73/159 |
| 4,866,984 A * | 9/1989 | Houghton | 73/159 |
| 4,936,140 A * | 6/1990 | Houghton et al. | 73/159 |
| 4,936,141 A * | 6/1990 | Anderson et al. | 73/159 |

(Continued)

FOREIGN PATENT DOCUMENTS

| | | |
|---|---|---|
| DE | 102009009826 A1 | 2/2009 |
| EP | 1790605 B1 | 5/2007 |

OTHER PUBLICATIONS

L&W Bending Tester, Lorentzen & Wettre, Kista, Sweden, retrieved from http://l-w.com.datakultur.net/index.php?paqe=shop.product_details&flypaqe=flypaqe.tpl&product_id=45&category_id=23&option=com_virtuemart&Itemid=53&lang=en on Nov. 8, 2012, pp. 1.

(Continued)

*Primary Examiner* — Lisa Caputo
*Assistant Examiner* — Jonathan Dunlap
(74) *Attorney, Agent, or Firm* — Muncy, Geissler, Olds & Lowe, P.C.

(57) ABSTRACT

A method, and apparatus, for determining bend resistance of a sample includes applying a weight to a sample and measuring an amount of deflection of the sample caused by applying the weight. The sample is provided on a sample holder and an initial position of the sample is measured with respect to the sample holder. A weight is applied to the sample and a change in position from the initial position to a deflection position of the sample due to the weight applied to the sample is measured. An amount of deflection of the sample is determined by dividing the change in position by the basis weight.

10 Claims, 9 Drawing Sheets

(56) References Cited

U.S. PATENT DOCUMENTS

| | | | |
|---|---|---|---|
| 4,970,895 A * | 11/1990 | Houghton et al. | 73/159 |
| 5,029,832 A | 7/1991 | Orsinger et al. | |
| 5,101,661 A * | 4/1992 | Cresson et al. | 73/159 |
| 5,111,688 A * | 5/1992 | Houghton et al. | 73/159 |
| 5,125,642 A | 6/1992 | Orsinger et al. | |
| 5,138,878 A * | 8/1992 | Cresson et al. | 73/159 |
| 5,174,159 A | 12/1992 | Jacobsen et al. | |
| 5,394,247 A | 2/1995 | Vahey et al. | |
| 5,574,227 A | 11/1996 | Allan | |
| 5,575,078 A | 11/1996 | Moulton, III | |
| 5,678,447 A * | 10/1997 | Graff | 73/159 |
| 5,962,861 A * | 10/1999 | Fowler | 250/559.27 |
| 6,000,693 A | 12/1999 | Tranquilla | |
| 6,050,149 A | 4/2000 | Yoshizawa | |
| 6,053,052 A * | 4/2000 | Starostovic | 73/851 |
| 6,175,235 B1 | 1/2001 | Obama et al. | |
| 6,189,879 B1 | 2/2001 | Conner et al. | |
| 6,196,537 B1 | 3/2001 | Conner et al. | |
| 6,264,793 B1 | 7/2001 | Ojala et al. | |
| 6,405,152 B1 | 6/2002 | Hall et al. | |
| 6,413,275 B1 * | 7/2002 | Nguyen et al. | 623/2.13 |
| 6,581,456 B1 * | 6/2003 | Clark | 73/159 |
| 6,748,801 B2 * | 6/2004 | Clark | 73/159 |
| 6,772,628 B2 * | 8/2004 | Clark | 73/159 |
| 6,865,818 B2 | 3/2005 | Petrowich | |
| 6,881,972 B2 * | 4/2005 | Butikofer et al. | 250/559.29 |
| RE39,037 E | 3/2006 | Obama et al. | |
| 7,096,743 B2 * | 8/2006 | Vogel et al. | 73/849 |
| 7,152,861 B2 * | 12/2006 | Kawasaki | 271/262 |
| 7,162,932 B2 | 1/2007 | Jorkama | |
| 7,380,451 B2 * | 6/2008 | Kawasaki et al. | 73/159 |
| 7,451,982 B2 * | 11/2008 | Kawasaki et al. | 271/265.04 |
| 7,458,576 B2 * | 12/2008 | Kawasaki et al. | 271/265.04 |
| 7,583,413 B2 * | 9/2009 | Nojiri et al. | 358/3.24 |
| 8,121,391 B2 | 2/2012 | Duss | |
| 8,226,625 B2 * | 7/2012 | Turner et al. | 604/385.22 |
| 8,226,626 B2 * | 7/2012 | Turner et al. | 604/385.22 |
| 8,231,595 B2 * | 7/2012 | Turner et al. | 604/385.22 |
| 8,388,594 B2 * | 3/2013 | Turner et al. | 604/385.22 |
| 2003/0053090 A1 * | 3/2003 | Nojiri et al. | 358/1.9 |
| 2006/0016996 A1 * | 1/2006 | Kaneko et al. | 250/339.1 |
| 2006/0022400 A1 * | 2/2006 | Kawasaki et al. | 271/227 |
| 2006/0254367 A1 * | 11/2006 | Hellstrom | 73/828 |
| 2006/0275045 A1 * | 12/2006 | Kawasaki et al. | 399/45 |
| 2014/0276517 A1 * | 9/2014 | Chester et al. | 604/372 |

OTHER PUBLICATIONS

Case Paper, Paper Thicknes (Caliper) Chart, Harrison, NY, retrieved from http://www.casepaper.com/resources/calculators/paper-thickness-caliper/ on Nov. 8, 2012, pp. 1-4.

Pearl Lewis, eHow Contributor, "How to Use a Paper Thickness Gauge," retrieved from http://www.ehow.com/how_7353829_use-paper-thickness-gauqe.html on Nov. 8, 2012, pp. 1-2.

\* cited by examiner

DEFLECTION INDICATION GAUGE

BACKGROUND OF THE INVENTION

1. Field of the Invention

The present invention relates to a measuring apparatus and method and more particularly to an apparatus and method for measuring an amount of deflection of a sample.

2. Description of the Background Art

Paper type is an important factor for all printing jobs as different types of paper have different properties and characteristics. The properties and characteristics of the paper type determine the capabilities and limitations of the paper type and, ultimately, the applicability of the paper type for a particular printing job.

One such property is stiffness or bending resistance. Thicker paper types are typically stiffer and paper is typically stiffer in the grain-short direction.

Bending resistance is of particular concern in printer paper applications as bending resistance can affect printer jamming characteristics of the paper. That is, the less flexible paper is (increased bending resistance), the greater the likelihood that the paper will jam in a printer.

Currently, no devices or methods exist for quickly and cost-effectively measuring the bending resistance of paper (e.g., printer paper).

SUMMARY OF THE INVENTION

In view of the foregoing and other exemplary problems, drawbacks, and disadvantages of the conventional methods and structures, an exemplary feature of the present invention is to provide a quick and cost effective method (and device) for measuring the bending resistance of paper.

In accordance with a first exemplary, non-limiting aspect of the present invention, a method includes providing a sample on a sample holder, measuring an initial position of the sample with respect to the sample holder, applying a weight to the sample, measuring a change in position from the initial position to a deflection position of the sample due to the weight applied to the sample, and determining an amount of deflection of the sample based on the change in position and a basis weight of the sample.

In accordance with a second exemplary, non-limiting aspect of the present invention, an apparatus includes a sample holder configured to receive a sample, a gauge configured to measure a position of the sample, and a weight adapted to be placed on the sample. The sample holder includes first and second edges on opposite sides of the sample holder and an open space disposed between the first and second edges such that the sample is supported on each of the edges and disposed over the open space. An initial position of the sample on the sample holder is measured using the gauge and a change in position is measured by the gauge after the weight is placed on the sample.

In accordance with a third exemplary, non-limiting aspect of the present invention, an apparatus includes a sample holder, a gauge positioned adjacent the sample holder, and a weight removably contained within a weight holder. The sample holder includes first and second edges disposed on opposites sides of the sample holder and an open space disposed between the first and second edges.

According to certain exemplary aspects of the invention, the sample includes paper. More particularly, the sample includes printer paper. According to certain exemplary embodiments of the invention, the sample includes a single piece of paper. However, the sample may include a stack of multiple sheets of paper, which may be measured simultaneously. The apparatus and method described above may be used to determine a characteristic of the paper, which correlates to printer jamming.

According to certain exemplary aspects of the invention, the method further includes determining a basis weight of the sample. As indicated above, the basis weight of the sample is used to determine the deflection value (CP). Specifically, the deflection value is determined using the following formula:

$$CP = \frac{\text{bar weight } (mN) \times \Delta \text{ distance (mm)}}{\text{Basis weight}\left(\frac{\text{gram}}{\text{m}^2}\right)}.$$

According to certain exemplary aspects of the invention, the method further includes applying a plurality of different weights to the sample. The change in position and amount of deflection are measured and determined for each of the plurality of weights. Additionally, one or more of the weights may be left on the sample for a set amount of time to determine the effect of time on the amount of deflection.

According to certain exemplary aspects of the invention, when measuring the change in position from the initial position of the sample due to the weight applied to the sample, the gauge is positioned at a lowest point of the sample on the sample holder. Accordingly, a maximum amount of deflection can be measured.

According to certain exemplary aspects of the invention, providing the sample on the sample holder further includes cutting the sample to a fixed dimension. Furthermore, the sample is then placed on the sample holder based on a direction in which sample deflection is to be tested.

According to certain exemplary aspects of the invention, the apparatus described above further includes a sample holding plate adjustably mounted above the sample holder. The sample holding plate includes a flat main body plate and an opening in the flat main body plate, where the opening is configured to receive the weight.

According to certain exemplary aspects of the invention, the sample is supported on only each of the edges and disposed over the open space.

Accordingly, the present invention provides the ability to determine a paper characteristic, which correlates to printer jamming. The method (and apparatus) of the present invention is able to distinguish the difference between "bad" and "good" paper product in terms that relate to jamming.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, do limit the present invention, and wherein.

DETAILED DESCRIPTION OF EXEMPLARY EMBODIMENTS OF THE PRESENT INVENTION

Figure 1:
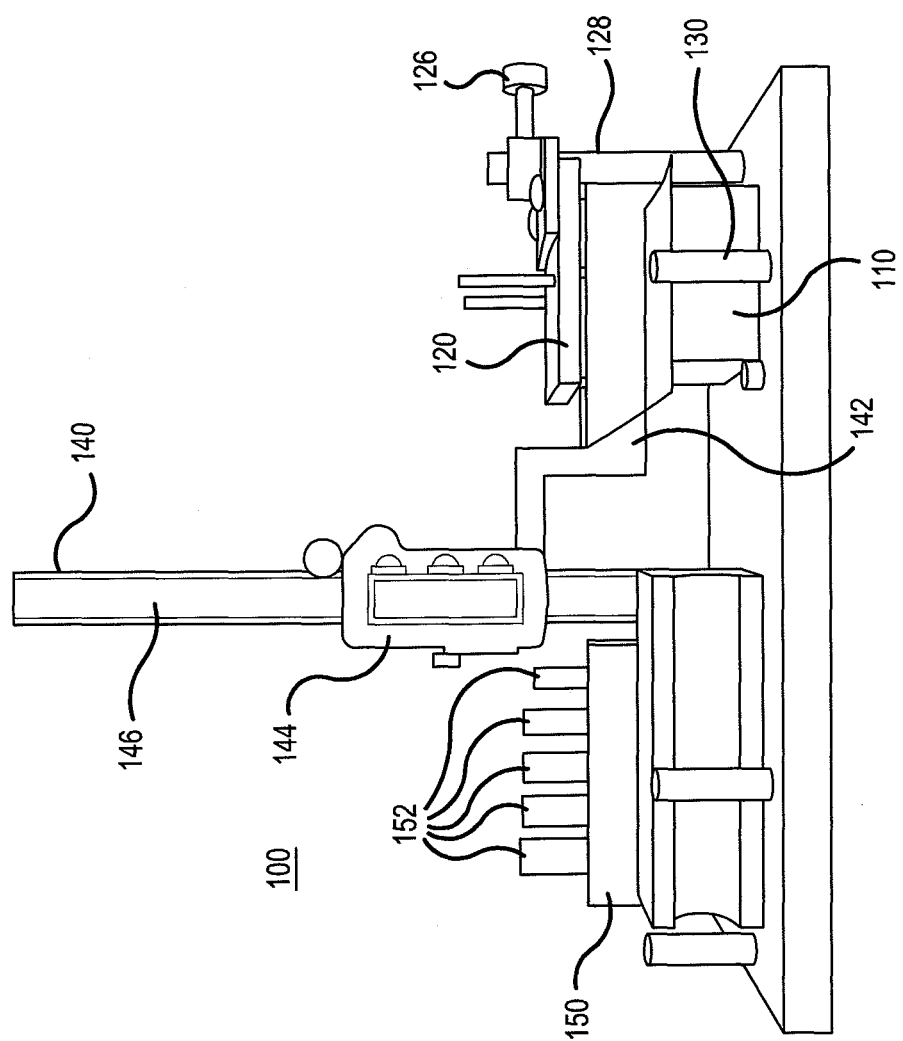
FIG. 1 illustrates a front view of an apparatus 100 according to an exemplary embodiment of the present invention.

Referring now to the drawings, and more particularly to FIGS. 1-8, there are shown exemplary embodiments of the method and structures according to the present invention.

Exemplary embodiments of the present invention are directed to a method (and apparatus) for measuring a sample to determine its bend resistance. According to certain exemplary embodiments of the invention, the sample includes various types of paper (e.g., printer paper). The use of the present invention is not limited to printer paper. Indeed, the present invention can be used to measure the bend resistance of any generally flat material including, but not limited to, plastic, metal, various types of paper, paper products, carboard, etc.

Figure 2:
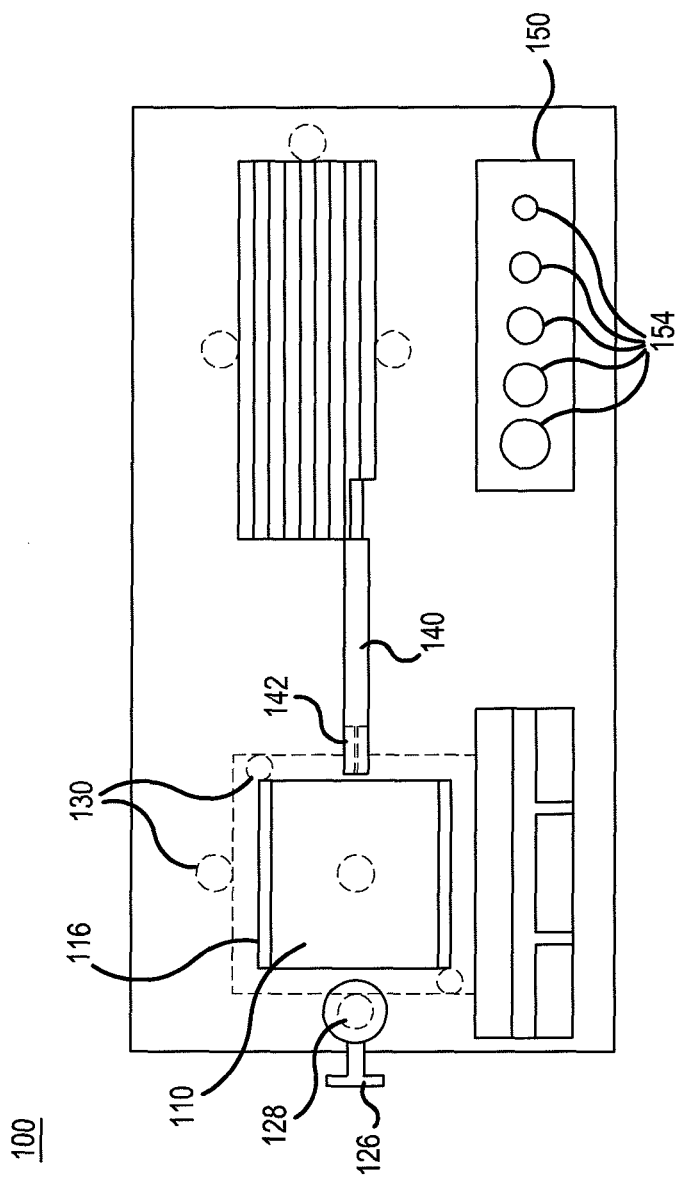
FIG. 2 illustrates a plan view with the apparatus 100 illustrated in FIG. 1 rotated 180°.
Figure 3:
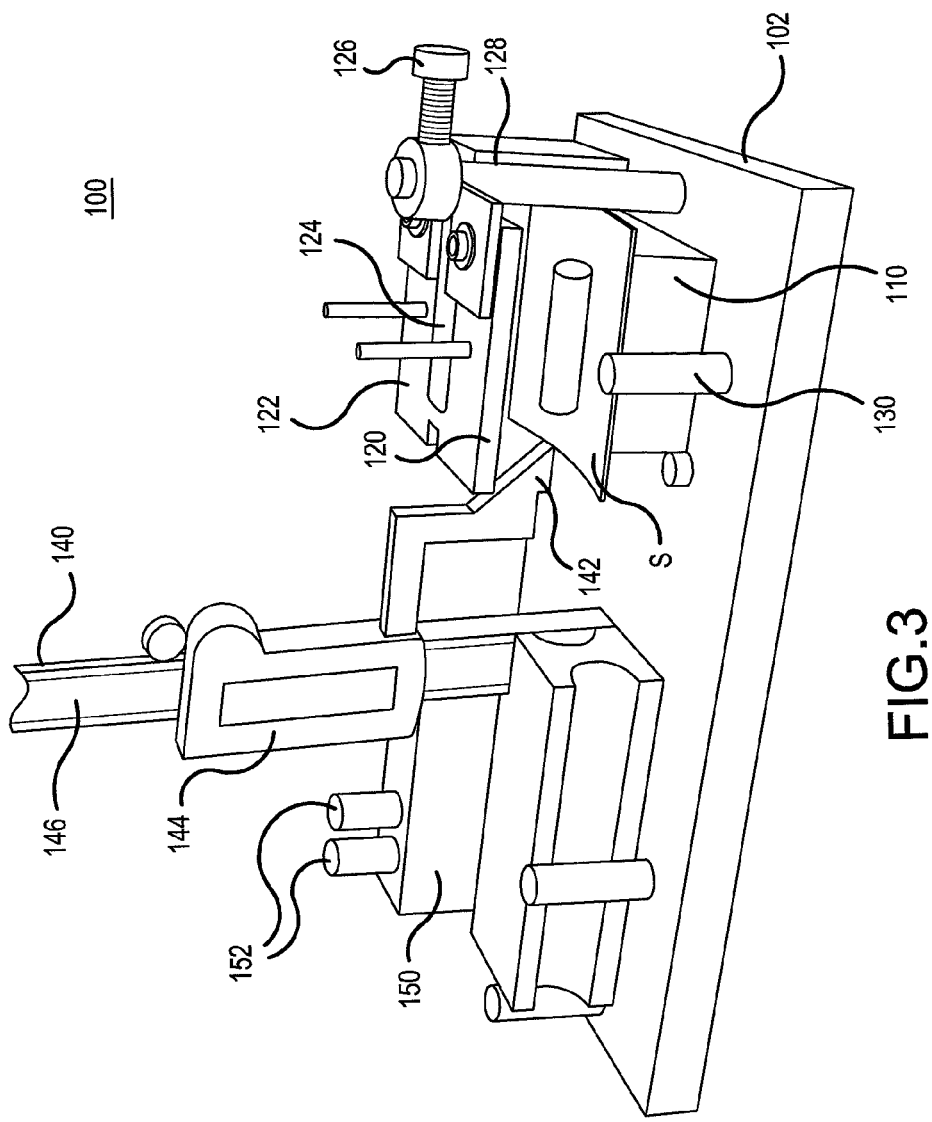
FIG. 3 illustrates a top perspective view of the apparatus 100 illustrated in FIG. 1.

FIGS. 1-3 illustrate a front view, a plan view, and a top view, respectively, of an apparatus 100 according to certain exemplary embodiments of the present invention. The apparatus 100 includes a sample holder 110, which is configured to support a sample to be measured by the apparatus. The sample holder 110 is disposed on a base 102 of the apparatus 100. According to certain exemplary embodiments of the present invention, the sample S is a piece of paper and, more specifically, printer paper.

Figure 4:
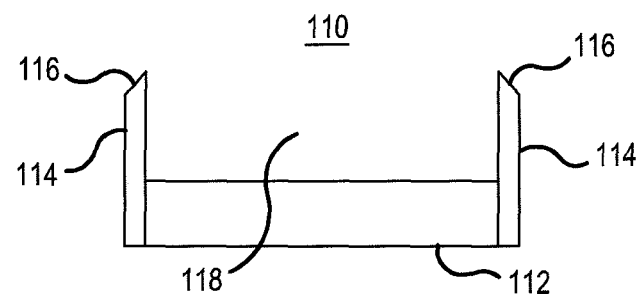
FIG. 4 illustrates an end view of a sample holder 110 of the apparatus 100 illustrated in FIGS. 1-3.

As is more clearly illustrated in FIG. 4, the sample holder 110 includes a bottom base portion 112 and two vertically extending side portions 114, which are disposed on opposite sides of the sample holder 110. First and second edges 116 are disposed at a top of the two vertically extending side portions 114. An open space 118 is disposed between the side portions 114. The sample S is positioned such that opposing portions of the sample S are supported at the first and second edges 116. Specifically, the portions of the sample S are only supported at the first and second edges 116 such that the sample S is positioned over the open space 118. The sample S could be supported at its ends/edges or could be supported such that a portion of the sample S extends beyond one or more of the first an second edges 116.

The first and second edges 116 are thin, knife-edge layers. For example, the first and second edges have a thickness of 0.5 mm. This is important to allow the paper sample to deflect freely.

Referring again to FIGS. 1-3, the apparatus 100 further includes a sample holder plate 120 adjustably positioned above the sample holder 110. The sample holder plate 120 has a horizontally disposed generally flat rectangular main body 122. An elongate opening 124 is disposed in a generally central portion of the sample holder plate 120.

The sample holder plate 120 is adjustably mounted above the sample holder 110 by a vertically disposed support member 128. The sample holder plate 120 is vertically adjusted along the support member 128 by tightening and loosening an adjustment mechanism 126 disposed on the support member 128. The adjustment mechanism 126 is threadedly engagable with the support member. The adjustment mechanism 126 in FIGS. 1-3 is illustrated as a screw or bolt. However, any suitable adjustable connection mechanism may be used.

One or more edge guides 130 are disposed around the edges of the sample holder 110. The sample is placed on the sample holder 110 such that it contacts the edge guides 130 to ensure that the sample S is properly positioned on the sample holder 110.

A gauge 140 is positioned adjacent the sample holder 110. The gauge may be a vernier caliper gauge. However, any similar, suitable gauge may be used. The gauge 140 includes a gauge pointer 142, configured to be positioned such that the gauge pointer 142 contacts the sample S. Specifically, the gauge pointer 142 contacts an edge of the sample S. The gauge 140 also includes a gauge reader 144, configured to read a dimension related to the sample, which is obtained using the gauge 140. The gauge reader 144 is vertically, slidably adjustable along a vertically disposed measuring portion 146 of the gauge 140.

A weight holder 150 is disposed on the base 102 of the apparatus 100. In the embodiment illustrated in FIGS. 1-3, the weight holder 150 is positioned along an edge of the base 102 adjacent the gauge 140, however, the weight holder 150 may be located at any suitable position on the base 102 or separate from the base. The weight holder 150, as illustrated in FIG. 2, includes a plurality of openings 154. The plurality of openings 154 are of varying size and are configured to receive one or more weights having varying size and weight. As is illustrated in FIGS. 1 and 3, one or more weights 152 are removably held within the openings 154 of the weight holder 150. The weights 152 illustrated in the Figures are cylinderal weights, however, any suitably shaped weight may be used. The weights 152 each have a different weight and are configured such that they may be placed within the elongate opening 124 of the sample holder plate 120. The weights 152 are configured such that the may be placed within and pass through the elongate opening 124 onto a sample S positioned on the sample holder 110.

Figure 5:
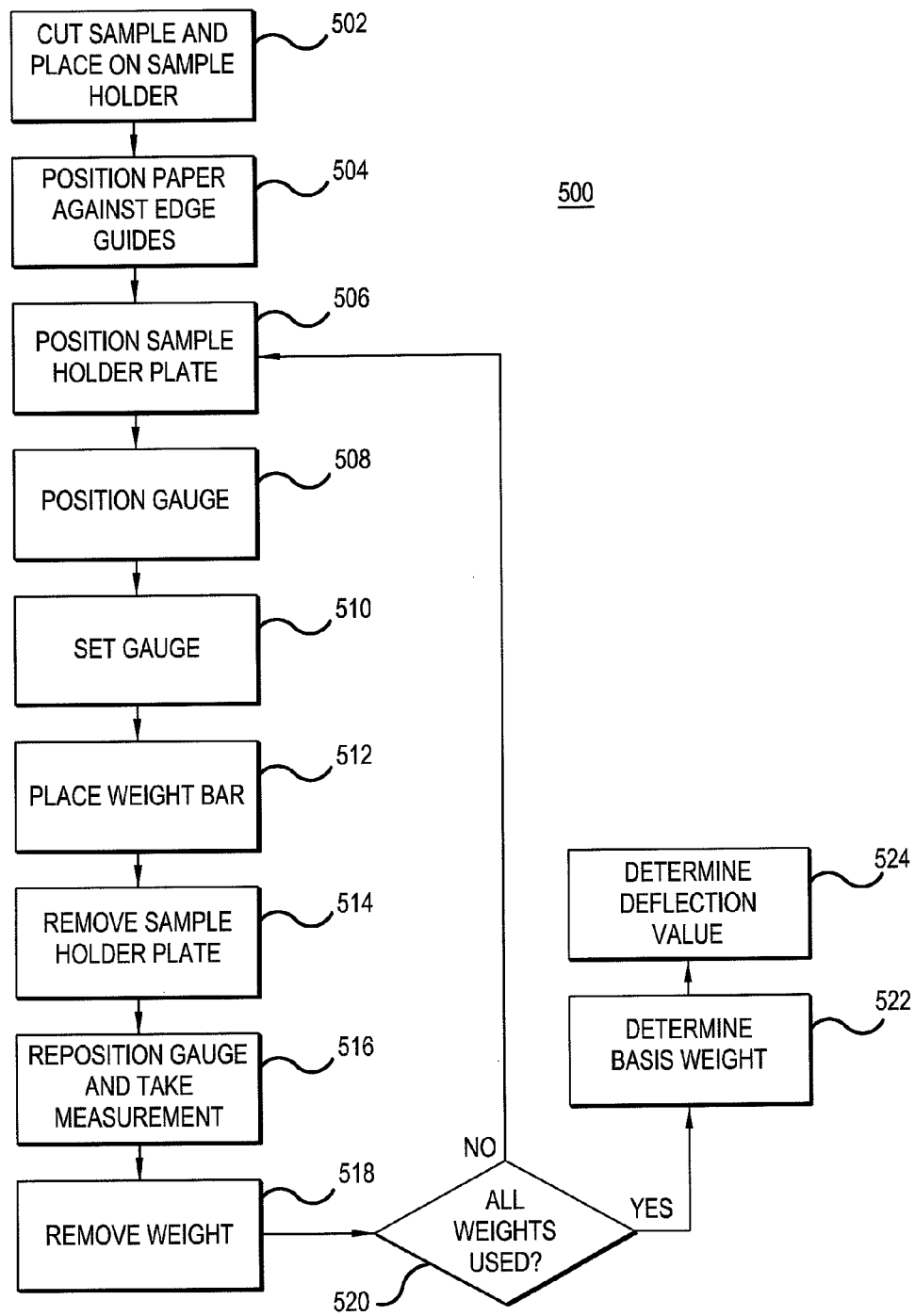
FIG. 5 illustrates a flow diagram for a method 500 according to an exemplary embodiment of the present invention.

FIG. 5 illustrates a flow diagram of a measurement method 500, using the apparatus described above with respect to FIGS. 1-4, according to certain exemplary embodiments of the present invention.

The method includes first cutting the sample S (502). The sample S is preferably cut to a fixed dimension. For example, in certain embodiments, the sample is cut to a 2"×2" sample size. This cutting step could be an optional step if an appropriately sized sample is already available. The fixed dimension of the sample is important for testing consistency. The sample S is then placed on the sample holder 110. The placement of the sample S on the sample holder 110 is dependent on the direction which the paper deflection is going to be tested, which include: Machine Direction and Cross Direction on both front and back sides.

Once the sample S is placed on the sample holder 110, the sample S is positioned (504) such that it touches the edge guides 130. The edge guides 130 provide proper placement of the sample S on the sample holder 110. The sample holder plate 120 is then lowered (506), by adjusting the adjustment mechanism 126, until the sample holder plate 120 contacts the sample S on the sample holder 110. The gauge 140 is then positioned such that the pointer 142 touches an edge of the sample S (508). Next, the measurement on the gauge reader 144 is zeroed (510). One of the plurality of weights 152 is selected and placed within the opening 124 on the sample holding plate 120 (512). The sample holding plate 120 is then removed by lifting it up along the support member 128 and tightening the adjustment mechanism 126 to hold the sample holding plate 120 in a raised position (514).

Figure 6A:
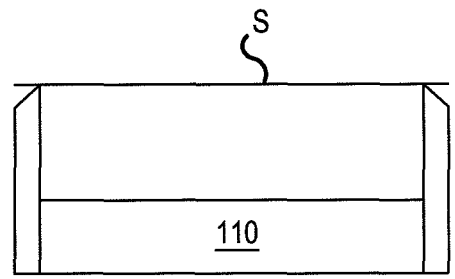
FIG. 6A illustrates a sample S positioned on the sample holder 110 without a weight on the sample S.
Figure 6B:
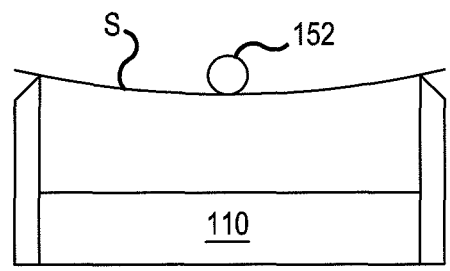
FIG. 6B illustrates a sample S positioned on the sample holder 110 with a weight on the sample S.

The gauge 140 is repositioned so it touches the sample S (516). When the weight is placed on the sample S, the sample S will deflect. That is, FIG. 6A illustrates the sample before a weight is placed on the sample S. FIG. 6B illustrates the sample when a weight is placed on the sample. Due to the weight on the sample S, the sample S will deflect a certain distance. The pointer 142 of the gauge 144 is positioned at the lowest point of the sample S, while the weight is positioned on the sample S, to determine the amount of deflection caused by the weight. The deflected position of the sample S is measured using the gauge reader 144.

Once the deflection is measured, the weight is removed from the sample S (518). The above method is repeated for each of the weights (520). Once all of the weights have been applied, the basis weight of the sample S is determined (522). The basis weight (gsm) is determined by measuring 1 square meter of the respective sample's mass (grams). The sample deflection value is then determined (524) by dividing the distance measured at the lowest point of the sample by the basis weight of the sample. Specifically, the following formula may be used to determine the deflection value (CP):

$$CP = \frac{\text{bar weight } (mN) \times \Delta \text{ distance (mm)}}{\text{Basis weight}\left(\frac{\text{gram}}{m^2}\right)}$$

The apparatus and method described above can be used to measure the bend resistance of a sample S. According to certain exemplary embodiments, the sample S is paper and, more particularly, printer paper. Printer paper that is less flexible (i.e., higher bend resistance) is more likely to cause a printer jam. Accordingly, a higher degree of deflection is desirable. The flexibility of paper depends on (but not limited to) basis weight, fiber orientation and softwood/hardwood ratio.

Figure 7A:
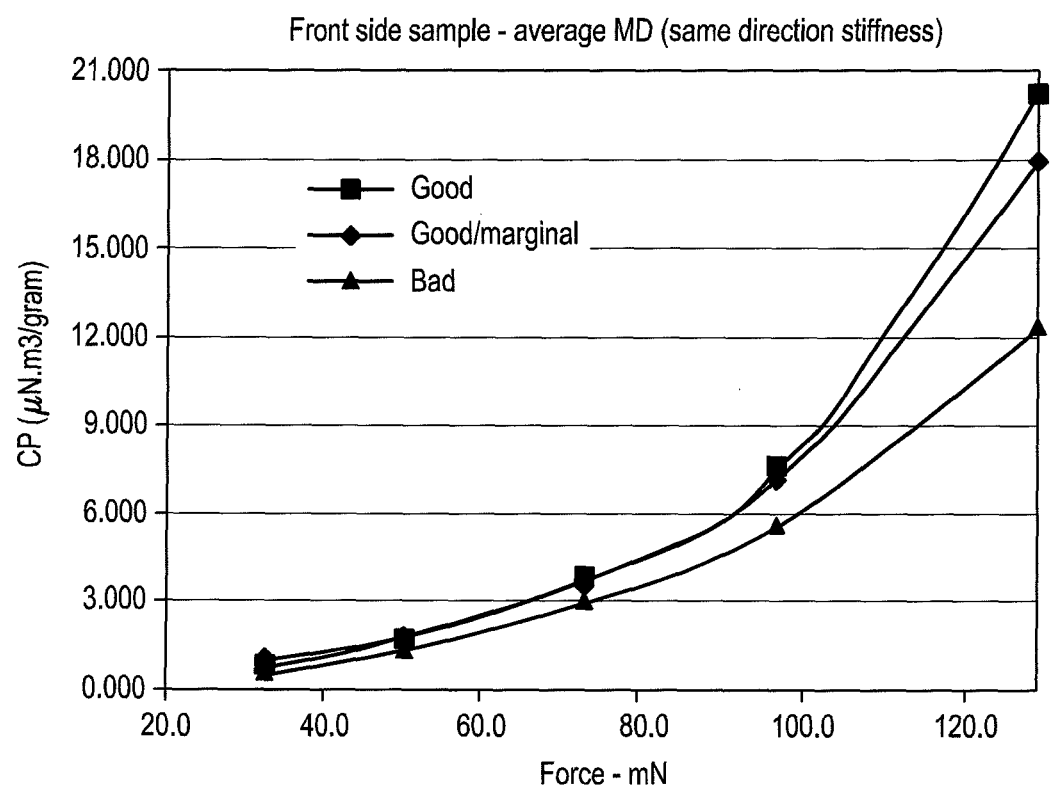
FIG. 7A is a graphical representation of the deflection amount of several front side samples.
Figure 7B:
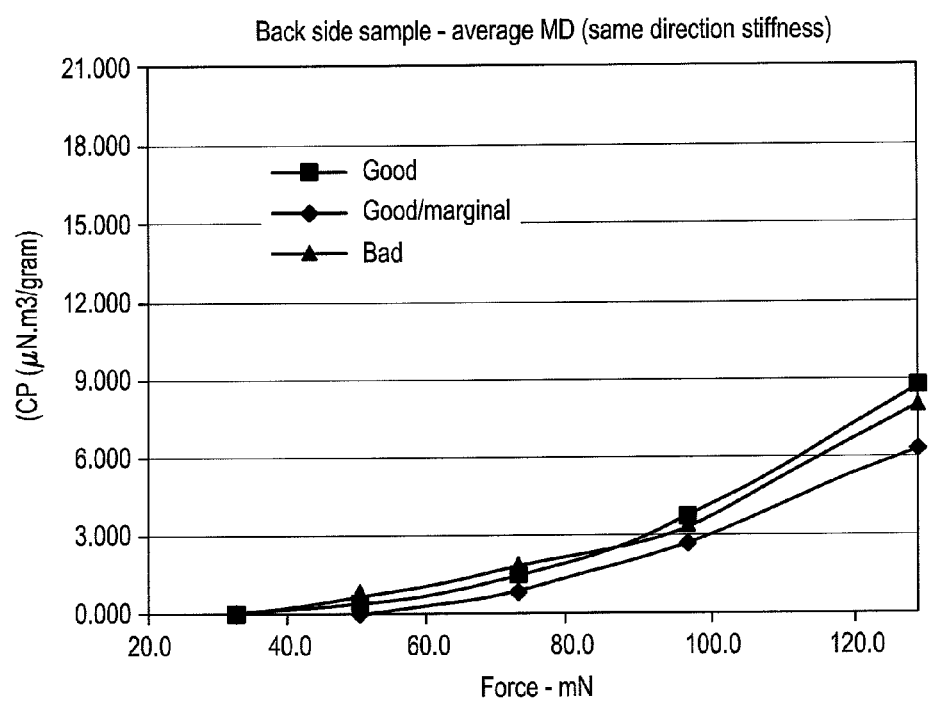
FIG. 7B is a graphical representation of the deflection amount of several back side samples.

FIGS. 7A and 7B provide a graphical representation of the amount of deflection (CP) versus the amount of force (mN) for three front side samples. The three samples include "bad", "marginal" and "good" samples. The sample category is based on the printer jamming studies. The higher CP value indicates that the sample is more flexible. That is, the higher CP value indicates that the sample is easier to deflect or bend. In FIG. 7A it is clear that the "bad" sample is less flexible compared with the "good" or "good/marginal" samples. The difference in CP value is more apparent when a higher force (i.e., a larger weight) is applied. FIG. 7B illustrates, that in the back side samples, the three samples have similar bending flexibility. With respect to FIGS. 7A and 7B, the front side refers to the side where the thermal coating is applied. The back side has no thermal coating. The sample is printed on the front side. However, at the high force values, the "good" sample still exhibits a larger CP value than the "bad" sample. Accordingly, as is illustrated in FIGS. 7A and 7B, the present invention is able to identify samples that are less likely to cause printer jamming (i.e., the "good" samples) and those that are more likely to cause printer jamming (i.e., the "bad" samples).

Figure 8:
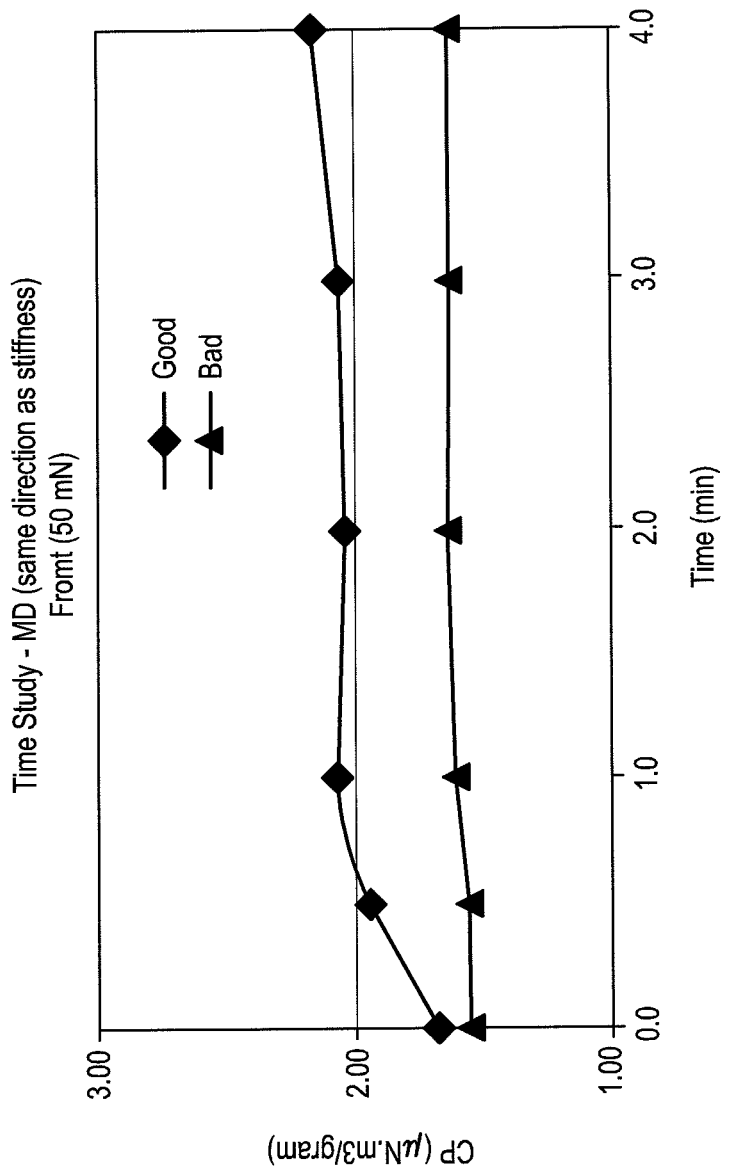
FIG. 8 is a graphical representation of the amount of deflection over time.

FIG. 8 provides a graphical representation of the effects of time on the amount of deflection of the sample. In the study in FIG. 8, a constant weight (e.g., 50 mN) was applied to two samples and the weight was left on the samples for a continuous amount of time to determine whether the samples would continue to deflect over time. As is clear from FIG. 8, the "good" sample continues to deflect over time. The "bad" sample, however, does not continue to deflect over time.

Accordingly, in the application of printer paper, the present inventive method and apparatus are able to determine whether a sample stock of paper is more or less likely to cause jamming in a printer by measuring the amount of deflection when a weight is applied to the sample.

While the invention has been described in terms of several exemplary embodiments, those skilled in the art will recognize that the invention can be practiced with modification within the spirit and scope of the appended claims. Such variations are not to be regarded as a departure from the spirit and scope of the invention, and all such modifications as would be obvious to one skilled in the art are to be included within the scope of the following claims.

Further, it is noted that, Applicant's intent is to encompass equivalents of all claim elements, even if amended later during prosecution.

What is claimed is:

1. A method, comprising:
providing a sample on a sample holder;
measuring an initial position of the sample with respect to the sample holder;
applying a weight to the sample;
measuring a change in position from the initial position to a deflection position of the sample due to the weight applied to the sample; and
determining an amount of deflection of the sample based on the change in position and a basis weight of the sample,
wherein the amount of deflection is determined using the following formula: (weight applied to the sample× change in position of sample)/basis weight of the sample.

2. The method according to claim 1, wherein the sample comprises paper.

3. The method according to claim 1, wherein the sample comprises printer paper.

4. The method according to claim 1, wherein the sample comprises a single sheet of paper.

5. The method according to claim 1, further comprising determining the basis weight of the sample.

6. The method according to claim 1, further comprising applying a plurality of different weights to the sample in series.

7. The method according to claim 6, wherein said measuring the change in position from the initial position to the deflection position of the sample due to the weight applied to the sample and said determining the amount of deflection of the sample by dividing the change in position by the basis weight of the sample are each repeated for each of the plurality of weights.

8. The method according to claim 1, wherein said measuring the change in position from the initial position to the deflection position of the sample due to the weight applied to the sample comprises positioning a gauge at a lowest point of the sample on the sample holder.

9. The method according to claim 1, wherein said providing the sample on the sample holder comprises cutting a sample to a fixed dimension.

10. The method according to claim 1, further comprising determining a placement of the sample on the sample holder based on a direction in which sample deflection is to be tested.

* * * * *